United States Patent [19]

Giannessi et al.

[11] Patent Number: 5,061,725
[45] Date of Patent: Oct. 29, 1991

[54] (PYRROLIDIN-2-ONE-1-YL) ACETAMIDES AND ENHANCERS OF LEARNING AND MEMORY PHARMACEUTICAL COMPOSITIONS COMPRISING SAME

[75] Inventors: Fabio Giannessi; Orlando Ghirardi; Domenico Misiti; Maria O. Tinti, all of Rome; Carlo Sclolastico, Milan, all of Italy

[73] Assignee: Sigma-Tau Industrie Farmaceutiche Riunite S.p.A., Rome, Italy

[21] Appl. No.: 551,951

[22] Filed: Jul. 12, 1990

[30] Foreign Application Priority Data

Jul. 12, 1989 [IT] Italy .................. 48180 A/89

[51] Int. Cl.$^5$ ............. A61K 31/40; A61K 31/44; C07D 401/00; C07D 207/27
[52] U.S. Cl. .................. 514/424; 514/91; 514/235.8; 514/255; 514/336; 548/112; 548/543; 548/544; 548/550; 546/281; 544/142; 544/372
[58] Field of Search ............ 514/424, 91, 235.8, 514/255, 336; 548/544, 121, 543, 544, 550; 546/281; 544/141, 372

[56] References Cited

U.S. PATENT DOCUMENTS

| | | | |
|---|---|---|---|
| 4,341,790 | 7/1982 | Betzing et al. | 514/424 |
| 4,581,364 | 4/1986 | Weber et al. | 514/424 |
| 4,833,140 | 5/1989 | Gobert et al. | 514/424 |
| 4,837,223 | 6/1989 | Gobert et al. | 514/424 |

Primary Examiner—David B. Springer
Attorney, Agent, or Firm—Oblon, Spivak, McClelland, Maier & Neustadt

[57] ABSTRACT (Pyrrolidin-2-one-1-yl)acetamides of general formula (I)

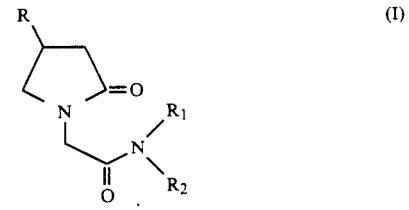

wherein R is hydrogen or hydroxyl, $R_1$ is hydrogen, $R_2$ is selected from the group consisting of:
2-aminoethyl,
2-(N,N-diisopropyl) aminoethyl,
3-(pyrrolidin-2-one-1-yl) propyl,
2-[N-(pyrrolidin-2-one-1-yl) acetyl] aminoethyl,
2-hydroxyethyl,
(glycerophosphorylethanolamino) carbonylmethyl,
1-trimethylammonium-3-carboxy-2-propyloxy-carbonylmethyl chloride,
(prolinol-1-yl) carbonylmethyl,
1-trimethylammonium-3-carboxyisopropyl), and
3-pyridylcarbamide;

or $R_1$ and $R_2$ taken together, are such as to form a cycle of formula

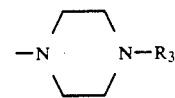

wherein $R_3$ is selected from the group consisting of phenyl substituted with halogens or halogen-substituted lower ($C_1$–$C_4$) alkyls and 4-morpholinocarbonylmethyl are potent enhancers of learning and memory.

Orally or parenterally administrable pharmaceutical compositions in unit dosage form comprise from about 100 to 500 mg of one of the compound of formula (I).

17 Claims, No Drawings

(PYRROLIDIN-2-ONE-1-YL) ACETAMIDES AND ENHANCERS OF LEARNING AND MEMORY PHARMACEUTICAL COMPOSITIONS COMPRISING SAME

The present invention relates to (pyrrolidin-2-one-1-yl) acetamides of general formula (I)

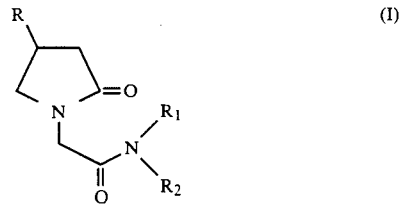

wherein R is hydrogen or hydroxyl, $R_1$ is hydrogen, $R_2$ is selected from the group consisting of:
2-aminoethyl,
2-(N,N-diisopropyl) aminoethyl,
3-(pyrrolidin-2-one-1-yl) propyl
2-[N-(pyrrolidin-2-one-1-yl) acetyl] aminoethyl,
2-hydroxyethyl,
(glycerophosphorylethanolamino) carbonylmethyl,
1-trimethylammonium-3-carboxy-2-propyloxy-carbonylmethyl chloride,
(prolinol-1-yl) carbonylmethyl,
1-trimethylammonium-3-carboxyisopropyl, and
3-pyridylcarbamide;
or $R_1$ and $R_2$, taken together, are such as to form a cycle of formula

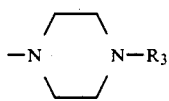

wherein $R_3$ is selected from the group consisting of phenyl substituted with halogens or halogen-substituted lower ($C_1$-$C_4$) alkyls and 4-morpholinocabonylmethyl. The compounds (I) are potent enhancers of learning and memory.

The present invention also relates to orally or parenterally administrable pharmaceutical compositions for enhancing learning and memory, comprising a novel compound of formula (I) as active ingredient.

The known compounds that from the structural and pharmacological viewpoint are the closest ones to the compounds of general formula (I) are piracetam (cfr. e.g. Curr. Dev. Psycopharmacol. 3, 22, 1976) and oxiracetam (cfr. e.g. Il Farmaco. Ed. Sc. 39/1, 16, 1984).

As illustrated hereinbelow, the compounds of the present invention are more potent than the known compounds.

The compounds of formula (I) are prepared via a process illustrated in the following synthesis scheme.

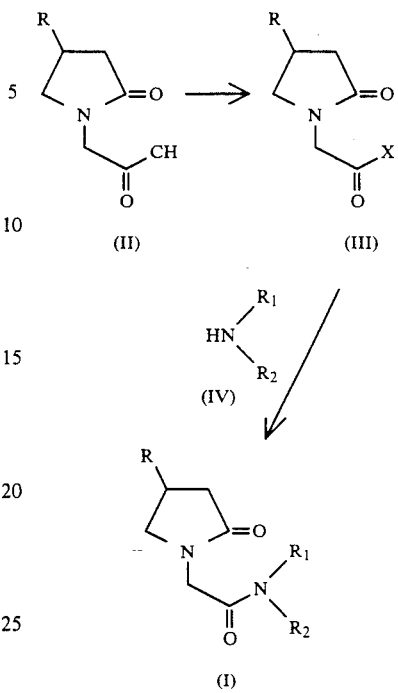

Pyrrolidin-2-one-1-yl acetic acid (II), substituted—if need be—at position 4, is converted into the activated compound (III) (X=activating group) with a halogenating agent such as thionyl chloride or oxalyl chloride, or a condensating agent such as dicyclohexylcarbodiimide (DCC), carbonyldiimidazole (CDI), 2-ethoxy-1-ethoxy-carbonyl-1,2-dihydroquinoline (EEDQ) or is activated as a short-chain alkyl ester. The activated compound (III) is reacted with a stechiometric or excess amount of amine (IV) in a solvent-free phase or dissolved in an inert solvent such as acetonitrile or methylene chloride, or—if EEDQ is used as activating agent then acetonitrile-water.

The raw reaction product is purified by silica gel chromatography with $CH_2Cl_2$—MetOH, $CHCl_3$—MetOH or AcOEt—MetOH gradient.

The following non-limiting examples illustrate the preparation of some compounds of formula (I).

EXAMPLE 1

Preparation of (R,S)-N-(2-aminoethyl)-2-(4-hydroxy-pyrrolidin-2-one-1-yl) acetamide (ST 630)

Ethylendiamine (8 g, 0.13 moles) was added to (R,S)-(4-hydroxy-pirrolidin-2-one-1-yl) ethyl acetate (2.4 g, 0.013 moles) (prepared as described in IT 1075280) and the mixture kept under stirring for 20 hours at room temperature. The excess amount of ethylendiamine was then evaporated under vacuum. The residue was chromatographed on silica gel using $CHCl_3$—MeOH as eluant, ratio 8:2.

Yield: 42%.
M.P.=99°-101° C.
TLC: silica gel: eluant; $CHCl_3/MeOH/NH_4OH/H_2O$ 55:35:5:5.
R.F.=0.25.
Elementary analysis ($C_8H_{15}N_3O_3$): Calculated (%): C 47.7; H 7.5; N 20.3. Found (%): C 47.3; H 7.5; N 20.8.
$^1H$ NMR (DMSO-$d_6$): δ7.85 (broad, 1H, 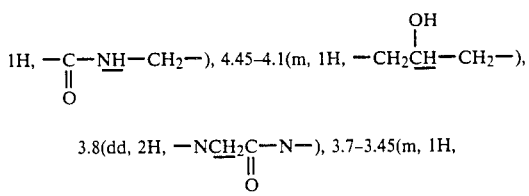 4.45-4.1(m, 1H, —CH₂CH—CH₂—), 3.8(dd, 2H, —NCH₂C—N—), 3.7-3.45(m, 1H,
               ‖
               O

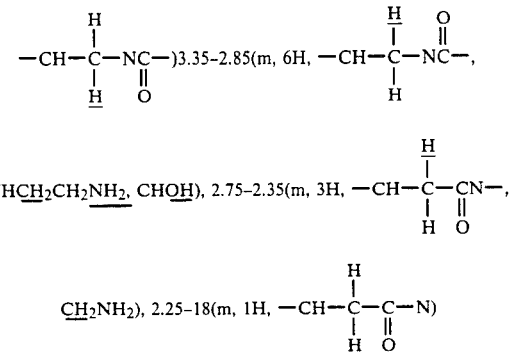 )3.35-2.85(m, 6H, —CH—C—NC—,

NHCH₂CH₂NH₂, CHOH), 2.75-2.35(m, 3H, —CH—C—CN—,

CH₂NH₂), 2.25-18(m, 1H, —CH—C—C—N)

EXAMPLE 2

Preparation of N-(2-aminoethyl)-2-(pyrrolidin-2-one-1-yl) acetamide (ST 645)

Ethylendiamine (5.73 g, 0.095 moles) was added to (pyrrolidin-2-one-1-yl) methyl acetate (5 g, 0.0318 moles) and the mixture was kept under stirring for 20 hours at room temperature. The raw reaction mixture was chromatographed on silica gel using CH₂Cl₂—MeOH as eluant, ratio 8:2.

Yield: 65%.
TLC: silica gel; eluant: CH₂Cl₂—MeOH 8:2.
R.F.: 0.1.
¹H NMR (CD Cl₃): δ7.6(broad,1H, —C—NH—CH₂—), 4(s, 2H, —NCH₂—C—NH), 3.75-3.15(m,
 ‖                                ‖
 O                                O 4H—CH₂—N—C—, C—NH—CH₂CH₂—), 2.8(t, 2H, —CH₂NH₂), 2.7-1.8(m, 6H, —CH₂CH₂—C—N—, —NH₂)
                                ‖
                                O HPLC
μ Bondapack —NH₂ L=300 mm inner diam. (i.d.)=3.9 mm size=10μ.
Eluant: CH₃CN—KH₂PO₄, 0.05M (65:35).
Flow rate: 1 ml/min.
Retention Time=6.89 min.

EXAMPLE 3

Preparation of N-(2-hydroxyethyl)-2-(pyrrolidin-2-one-1-yl) acetamide (ST 644)

Ethanolamine (1.943 g, 0.0318 moles) was added to (pyrrolidin-2-one-yl) methyl acetate (5 g, 0.0318 moles) and the mixture was kept under stirring for 20 hours at room temperature. The raw reaction mixture was chromatographed on silica gel using EtoAc—MeOH as eluant, ratio 8:2.

Yield: 70%.
M.P.: 52°-54° C.
TLC silica gel; eluant: EtOAc/MeOH 8:2.
R.F.: 0.2.
Elementary analysis: (C₈H₁₄N₂O₃): Calculated (%) C 51.6; H 7.58; N 15.04. Found (%) C 50.82; H 7.63; N 14.9.
¹H NMR (CDCl₃): δ7.4(broad, 1H, —CNHCH₂—), 4.1(s, 1H, —CH₂OH), 4(s, 2H, —NCH₂C—NH—), 3.8-3.2(m, 6H, —CH₂NC—,

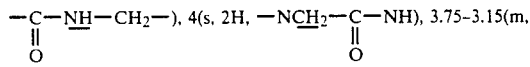

HPLC
μ Bondapack —NH₂, L=300 mm, i.d.=3.9 mm, size 10μ.
eluant: CH₃CN—KH₂PO₄ 0.05M (65:35).
Flow rate: 1 ml/min.
Retention Time=3.67 min.

EXAMPLE 4

Preparation of (R,S)-N-[2-(N,N-diisopropyl) aminoethyl]-2-(4-hydroxy-pyrrolidin-2-one-1-yl) acetamide (ST 632)

2-(diisopropylamine) ethylamine (3.9 g, 0.027 moles) was added to (R,S)-(4-hydroxy-pyrrolidin-2-one-1-yl) ethyl acetate (5 g, 0.027 moles) and the mixture was kept under stirring for 60 hours at room temperature. The ethanol thus formed was separated by concentration under vacuum and the remaining oil was taken up with ethyl ether and kept under stirring until the product was precipitated as a white solid.

Yield: 60%.
M.P.: 67° C.
TLC: silica gel; eluant: AcOEt—MeOH—NH₄OH 8:2:0.1.
R.F.: 0.5.
¹H NMR (DMSO-d₆): δ7.7(broad,1H,

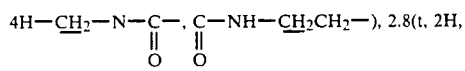

2H, —NCH₂—CNH—), 3.7-3.4(m, 1H, —CH—C—NC), 3.3-

1.8(9H, CH—C—NC—, CNHCH₂CH₂, —CHCH₂C—N—,

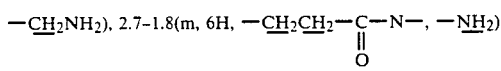

HPLC
μ Bondapack —NH₂, L=300 mm, i.d.=3.9 mm, size=10μ.
eluant: CH₃CN—KH₂PO₄, 0.05M (65:35).
Flow rate: 1 ml/min.
Retention Time=5.35 min.

EXAMPLE 5

Preparation of N-[3-(pyrrolidin-2-one-1-yl) propyl]-2-(pyrrolidin-2-one-1-yl) acetamide (ST 637)

1-(3-aminopropyl)-2 pyrrolidinone (4.523 g, 0.0318 moles) was added to (pyrrolidin-2-one-1-yl) methyl acetate (5 g, 0.0318 moles) and the mixture was kept under stirring for 20 hours at room temperature. The oil was chromatographed on $SiO_2$ using AcOEt—MeOH as eluant, ratio 95:5.

Yield: 54%.

M.P.: 56°–58° C.

TLC: silica gel; eluant: AcOEt—MeOH—$NH_4OH$ 9:1:0.1.

R.F.=0.2.

Elementary analysis ($C_{13}H_{21}N_3O_3$): Calculated (%) C 58.4; H 7.92; N 15.71. Found (%) C 58.12; H 8.14; N 15.4.

$^1$H NMR ($CDCl_3$): δ7.35(broad,1H,

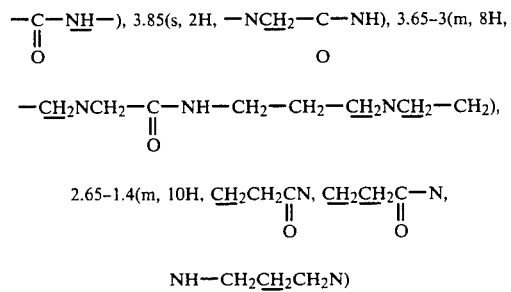

2.65–1.4(m, 10H, $\underline{CH_2}CH_2CN$, $\underline{CH_2}CH_2\underset{\underset{O}{\parallel}}{C}$—N, NH—$CH_2\underline{CH_2}CH_2N$)

HPLC

μ Bondapack —$NH_2$) L=300 mm, i.d.=3.9, size=10μ.

eluant: $KH_2PO_4$ 0.05M —$CH_3CN$ (35:65).

Flow rate: 1 ml/min.

Retention Time=4.27 min.

EXAMPLE 6

Preparation of (R,S)-N-[2-(4-hydroxy-pyrrolidin-2-one-1-yl) acetyl], N'[2-(pyrrolidin-2-one-1-yl)acetyl] ethylendiamine (ST 636)

DCC (1.031 g, 0.005 moles) was added to (pyrrolidin-2-one-1-yl) acetic acid (0.715 g, 0.005 moles) in 50 ml of acetonitrile and kept under stirring for one hour at room temperature. ST 630 (1.006 g, 0.005 moles) was then added and the mixture kept under stirring for 20 hours and filtered. The dried filtrate was chromatographed on silica gel using AtOAc—MeOH as eluant, ratio 6:4.

Yield: 70%.

M.P.: 147°–148° C.

TLC: silica gel; eluant: EtOAc—MeOH 6:4.

R.F.: 0.3.

Elementary analysis ($C_{14}H_{22}N_4O_5$): Calculated (%) C 51.5; H 6.8; N 17.1. Found (%) C 51.3; H 6.9; N 16.7.

$^1$H NMR (DMSO-$D_6$): δ8(broad,2H,

2C<u>NH</u>) 4.6–4.2(m, 2H, —<u>CHOH</u>)4.1–3(m, 12H,

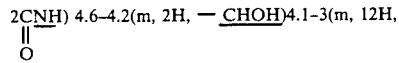

2.75–1.75(m, 6H, —$\underline{CH_2}CH_2CN$, —N$\underset{\underset{O}{\parallel}}{C}$—$\underline{CH_2}CHOH$)

HPLC

μ Bondapack —$NH_2$, L=300 mm, i.d.=3.9 mm, size=10μ.

eluant $CH_3CN$—$KH_2PO_4$ 0.05M (65:35).

Flow rate: 1 ml/min.

Retention Time=9.17 min.

EXAMPLE 7

Preparation of N-nicotinoyl,N'-[pyrrolidin-2-one-1-yl) acetyl] hydrazine (ST 631)

CDI (4.1 g, 0.025 moles) was added to (pyrrolidin-2-one-1-yl) acetic acid (3 g, 0.021 moles) in 75 ml of $CH_2Cl_2$ and the mixture was kept under stirring for one hour at room temperature. Nicotinoylhydrazide (2.9 g, 0.021 moles) was added to the mixture and the solution kept under stirring for 20 hours at room temperature. The raw product obtained by evaporation of the solvent was chromatographed on silica gel using EtOAc—MeOH as eluant, ratio 9:1. The product thus obtained was crystallized from ethyl ether.

Yield: 30%.

M.P.: 137°–139° C.

TLC: eluant: EtOH—MeOH 7:3.

R.F.: 0.25.

Elementary analysis ($C_{12}H_{14}N_4O_3$): Calculated (%) C 54.91; H 5.32; N 21.37. Found (%) C 55.01; H 5.33; N 20.77.

$^1$HNMR ($D_2O$): δ8.2–8.55 (m,2H,aromatic), 8.3–9.05 (m,1H, aromatic), 7.8–7.4 (m,1H,aromatic), 4.2 (s,2H,

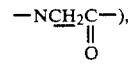

3.6(t,2H,—$CH_2CH_2$—N—)2.7–1.9 (m,4H,—$CH_2CH_2CH_2$—N—).

HPLC

μ Bondapack —$NH_2$, L=300 mm, i.d.=3.9 mm, size=10μ.

Eluant: $CH_3CN$—$KH_2PO_4$, 0.05M (65:35).

Flow rate: 1 ml/min.

Retention time: 3.9 min.

EXAMPLE 8

Preparation of 1-[2-(pyrrolidin-2-one-1-yl) acetyl-4-(3-trifluoromethylphenyl) piperazine (ST 638)

CDI (4.08 g, 0.025 moles) was added to 2.98 g (0.021 moles) of (pyrrolidin-2-one-1-yl) acetic acid in 70 ml of $CH_2Cl_2$ under stirring and after one hour N-(3-trifluoromethylphenyl) piperazine (3.94 ml, 0.021 moles) was added. The solution was kept under stirring for 20 hours at room temperature. The raw product obtained by evaporating the solvent was chromatographed on silica gel using $CHCl_3$—MeOH as eluant, ratio 95:5.

Yield: 89%.

M.P.: 115°–117° C.

TLC: silica gel; eluant $CHCl_3$—MeOH, 95:5.

R.F.: 0.65.

Elementary analysis ($C_{17}H_{20}F_3N_3O_2$): Calculated (%) C 57.45; H 5.67; N 11.82. Found (%) C 57.41; H 5.75; N 12.01.

1H NMR (CDCl3): δ7.35–6.75(m,4H,aromatic), 4.1(s,2H,

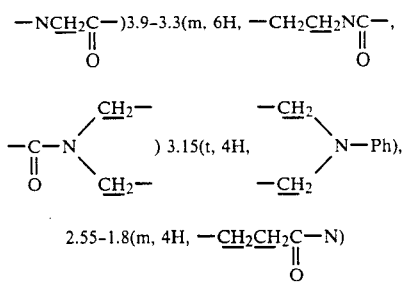

HPLC
Nova-pack —C18, L=100 mm, i.d.=5 mm, size=4μ.
Eluant: KH2PO4, 0.05M—CH3CN, (65.35).
Flow rate: 1 ml/min.
Retention time: 7.59 min.

EXAMPLE 9

Preparation of 1-[2-(pyrrolidin-2-one-1-yl) acetyl]-4-(3-chlorophenyl)piperazine (ST 682)

DCC (8.66 g, 0.042 moles) and N-(3-chlorophenyl) piperazine (8.26 g, 0.042 moles) were added to 6.0 g (0.042 moles) of (pyrrolidin-2-one-1-yl) acetic acid in 100 ml of CH2Cl2 and the mixture was refluxed for 6 hours. The solid thus obtained after filtration and evaporation of the solvent was chromatographed on silica gel using EtOAc—MeOH as eluant, ratio 95:5

Yield: 51%.
M.P.: 113°–114° C.
TLC: silica gel: eluant; EtOAC—MeOH 95:5.
R.F.: 0.14.
Elementary analysis (C16H20ClN3O2): Calculated (%) C 59.71; H 6.26; N 13.05. Found (%) C 59.64; H 6.34; N 12.84.

1H NMR (CDCl3): δ7.15–6.45(m,4H,aromatic), 4.05(s,2H,

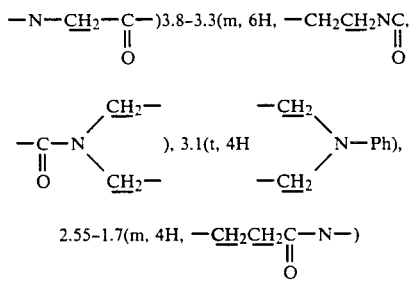

HPLC
Techopak —C18, L=300, i.d.=3.9 mm, size=10μ.
Eluant: KH2PO4, 0.05M—CH3CN, (65:35).
Flow rate: 1 ml/min.
Retention time: 9.72 min.

EXAMPLE 10

Preparation of 1-[2-(pyrrolidin-2-one-1-yl) acetyl]-4-(morpholinocarbonylmethyl) piperazine (ST 673)

CDI (2.43 g, 0.015 moles) was added to 1.72 g (0.012 moles) of (pyrrolidin-2-one-1-yl) acetic acid in 40 ml of CH2Cl2 under stirring and after one hour morpholinocarbonylmethyl piperazine 2.56 g, 0.012 moles) was added. The solution was kept under stirring for 20 hours at room temperature, the solvent was then evaporated and the residue chromatographed on silica gel using CHCl3—MeOH as eluant, ratio 95:5.

Yield: 45%.
M.P.: 123°–125° C.
TLC: silica gel EtOAc—MeOH 7:3.
R.F.: 0.15.
Elementary analysis (C16H26N4O4): Calculated (%): C 56.78; H 7.74; N 16.55. Found (%): C 56.48; H 7.93; N 16.38.

1H NMR (CDCl3): δ4.05 (s,2H,

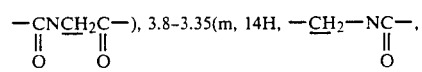

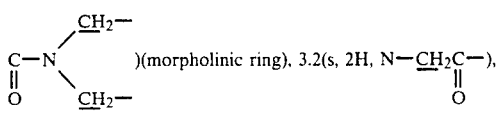

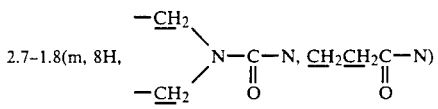

HPLC
μ Bondapack —NH2, L=300 mm, i.d.=3.9 mm, size=10μ.
Eluant: KH2PO4 0.05M—CH3CN (35:65).
Flow rate: 1 ml/min.
Retention time: 4.62 min.

EXAMPLE 11

Preparation of (S)-N-(prolinol-1-yl)carbonylmethyl-2-(pyrrolidin-2-one-1-yl)acetamide (ST 656)

EEDQ (9.89 g, 0.04 moles) and H2O until complete solubilization of the solution were added to 4 g (0.02 moles) of N-[2-pyrrolidin-2-one-1-yl)acetyl] glycine (prepared as described in UK 1539817) in 100 ml of CH3CN under stirring. After 30 min, S-prolinol (3.034 g, 0.03 moles) was added and the reaction mixture was kept under stirring for 60 hours at room temperature. The solvent was evaporated and the residue chromatographed on silica gel using EtOAc—MeOH as eluant, ratio: 8:2;

Yield: 35%.
[α] = −40.6° C. MeOH (C=1.8).
TLC: silica gel; eluant EtOAC—MeOH, ratio 8:2.
R.F.: 0.15.

1H NMR (CDCl3): δ7.3(broad, 1H,

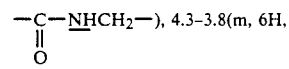

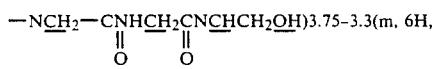

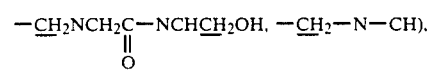

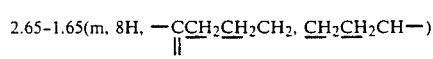

HPLC

μ Bondapack —C$_{18}$, L=300 mm, i.d.=3.9 mm, size=10μ.
Eluant: KH$_2$PO$_4$, 0.05M—CH$_3$CN, (80:20).
Flow rate: 1 ml/min.
Retention time: 3.53.

EXAMPLE 12

Preparation of (R,S)-N-(1-trimethylammonium-3-carboxyisopropyl)-2-(pyrrolidin-2-one-1-yl) acetamide (ST 650)

EEDQ (18.54 g, 0.075 moles) and H$_2$O up to complete solubilization of the mixture were added to 7.21 g (0.05 moles) of (pyrrolidin-2-one-1-yl) acetic acid in 150 ml of CH$_3$CN under stirring. After 30 min (R,S)-aminocarnitine dihydrochloride (9.8 g, 0.042 moles) (prepared as described in J. Biol. Chem. 269, 14748, 1985) and triethylamine (8.59 g, 0.084 moles) were added and the solution kept under stirring for 60 hours at room temperature.

The solvent was evaporated and the residue chromatographed on silica gel using EtOAC-MeOH as eluant, ratio 1:1. The product thus obtained was percolated on weak basic resin AMBERLIST A21 using methanol as eluant. The methanol was then evaporated and the product dissolved in H$_2$O was treated with activated carbon, filtered and lyophilized.

Yield: 30%.
M.P.: 168°–179° C. (with gas production).
TLC: silica gel, eluant CHCl$_3$—MeOH—NH$_4$OH—H$_2$O 55:35:5:5.
R.F.: 0.3.
$^1$H NMR (DMSO-D$_6$): δ8.8(d, 1H,

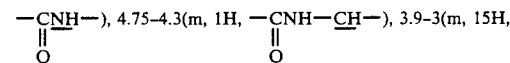

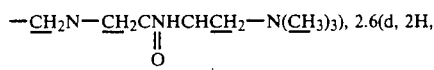

NHC$\underline{H}$CH$_2$COO)2.35-1.8(m, 4H, —C$\underline{H}_2$CH$_2$C—N)
                                            ‖
                                            O HPLC
μBondapack —NH$_2$, L=300 mm, i.d.=3.9 mm, size=10μ.
Eluant: CH$_3$CN—KH$_2$PO$_4$ 0.05M (65:35).
Flow rate: 1 ml/min.
Retention time: 13.27.

EXAMPLE 13

Preparation of L--N-(glycerophosphorylethanolaminocarbonylmethyl)2-(pyrrolidin-2-one-1-yl) acetamide (ST 625)

A solution of EEDQ (1.879 g, 7.59 μmoles) and N-[2-pyrrolidin-2-one-1-yl) acetyl] glycine (0.505 g, 2.53 moles) in THF (11 ml), H$_2$O (5.5 ml) and DMF (2 ml) was added to a solution of GFE (1.269 g, 4.43 μmoles) in H$_2$O (5.5 ml) and NEt$_3$ (0.553 g, 5.46 μmoles) under stirring at room temperature. The solution was kept for 60 hours at room temperature, extracted with CH$_2$Cl$_2$ (1×10 ml) and the aqueous phase evaporated under vacuum. The residue was chromatographed on a column (silica flash) using EtOH—H$_2$O as eluant, ratio 9:1. The resulting product was taken up with H$_2$O and percoated on strong acid resin DOWEX 50W. By evaporating to dryness the acid fractions, 705 g of product were obtained.

Yield: 70%
$^1$H NMR (D$_2$O): δ4-3.6(m,9H,

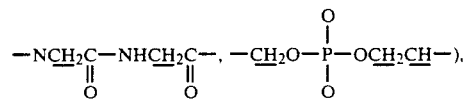

3.6-3.3(m, 6H, —C$\underline{H}_2$NC—, —NHC$\underline{H}_2$CH$_2$O—, CHC$\underline{H}_2$OH),
                ‖
                O 2.5-1.8(m, 4H, —C$\underline{H}_2$CH$_2$CN—)
                ‖
                O The product was characterized as calcium salt, obtained by dissolving 1 mmole ST 625 in H$_2$O and treating it with CaCO$_3$ (0.5 mmoles). The solution was evaporated under vacuum, the residue taken up several times with anhydrous EtOH and dried on P$_2$O$_5$ at 0.01 mmHg.

M.P.: 187°–190° C. (with dec.).
Elementary analysis (C$_{26}$H$_{46}$N$_6$O$_{18}$P$_2$Ca): Calculated (%) C 37.5, H 5.5, N 10.1. Found (%) C 37.9, H 5.6, N 9.8.

HPLC
μBondapack —NH2, L=300 mm, i.d.=3.9 mm, size=10μ.
Eluant: CH$_3$CN—KH$_2$PO$_4$ 0.05M (65:35).
Flow rate: 0.1 ml/min.
Retention time: 8:11 min.

EXAMPLE 14

Preparation of (R)-N-(1-trimethylammonium-3-carboxy-2-propyloxycarbonylmethyl)-2-(pyrrolidin-2-one-1-yl) acetamide chloride (ST 635)

CDI (2.675 g, 0.0165 moles) was added to a suspension of N-[2(pyrrolidin-2-one-1-yl)acetyl]glycine (3.007 g, 0.015 moles) in THF (30 ml) in a nitrogen atmosphere and under stirring at room temperature. After 30 min, carnitine benzylester perchlorate (2.642 g, 0.0075 moles) in THF (30 ml) was added and the reaction mixture kept at room temperature for 24 hours. The THF was decanted and the residue taken up 4 times with 25 ml THF that was removed every time by decantation. The residue taken up with MeOH was percolated on weak basic resin A21, eluting with MeOH. The product obtained by evaporation of the MeOH was taken up with EtOH and precipitated with ether. 10% Pd/C (0.464 g, 0.44 moles) was added to 2.062 g (4.4 mmoles) of the precipitate dissolved in H$_2$O. The mixture was hydrogenated at room temperature and pressure. After 6 hours, the Pd/C was filtered off and the filtrate evaporated to dryness was purified with preparative HPLC (Prepak column C$_{18}$; eluant H$_2$O—CH$_3$CN; 65:35).

Yield: 63%.
$^1$H NMR (D$_2$O): δ5 mm, 1H, —CHOH), 4.1(s, 4H,

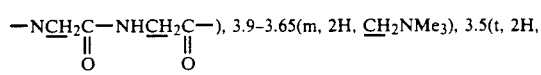

-continued

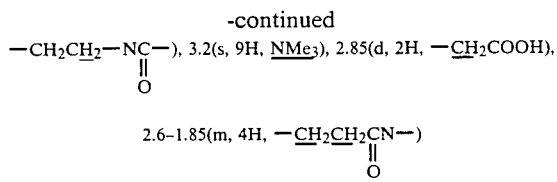

HPLC

μBondapack —$NH_2$, L=300 mm, i.d.=3.9 mm, size=10μ.

Eluant $CH_3CN$—$KH_2PO_4$ 0.05 (65:35).

Flow rate: 1 ml/min.

Retention time: 12.14 min.

The activity of the compounds of the invention was assessed in several pharmacological tests. Some of these tests wherein piracetam and oxiracetam were used as reference standards are illustrated hereinbelow.

(A) Assessment of the antiamnesic activity

In order to assess the antiamnesic activity the passive avoidance test in mice was used. Amnesia was brought about by administration of scopolamine (cfr. Bammer, Pharmacological investigations of neurotransmitter involvement in passive avoidance responding: a Review and some new results. *Neurosci. Biobehav. Rev.*, 6 (3) 247–296, 1982); or by electroconvulsive shock (ECS) (cfr. Banfi et al., A screening method for substances potentially active on learning and memory. *J. Pharmacol. Methods* Vol: 8 (4) 255–263, 1982 and Butler et al., Amnesia-reversal activity of a series of N[(disusbstituted-amino)alkyl]-2-oxo-1-pyrrolidineacetamides, including Pramiracetam. *J. Med. Chem.*, 27, N. 5, 684–691, 1984). Male albino CD1 mice (Charles River-Germany) fed on a normal diet, were used for the ECS-induced amnesia test. Male CD1 mice (Charles River-Italy) were used for the scopolamine-induced amnesia test. The compounds were administered i.p.; doses equimolar to 100, 10 and 1 mg oxiracetam $kg^{-1}$ were used.

The water-soluble compounds were dissolved in saline; the insoluble ones were dissolved in dimethylsulfoxide and then diluted in 2% Tween 80, ratio 1:4.

The apparatus for passive avoidance conditioning was a black plastic chamber (42×42 cm, height 40 cm) provided with a floor constructed of metal rods that could be electrified. From the front wall extended a white runway, 30 cm long and 10 cm wide provided with side walls 12 cm high, which led into the box through a guillotine door. The runway was lightened by a 60 W lamp (cfr. Ader et al., Retention of passive avoidance response as a function of the intensity and duration of electric shock. *Psychon. Sci.*, 26 (3), 125–127, 1972).

The animals, 30 minutes following treatment, were placed on the runway. After one minute of adaptation, the door was raised and the time employed by the animal to enter the darkened box with all four feet, was recorded.

Upon entry, the guillotine door was lowered and 5 seconds thereafter the rods were electrified, 0.24 mA for 2 seconds.

The mouse was then removed from the chamber and immediately administered an electroshock delivered through spring clips attached to the ears (square wave, intensity 20 mA, amplitude 0.6 msec, duration 0.5 s, frequency 50 Hz). Alternatively, in the scopolamine-induced amnesia test, the animals were administered the compounds under examination and scopolamine (1.0 mg/kg s.c.) 30 and 15 minutes, respectively, before they were placed on the runway. The test then continued as previously described. In both tests, retention was assessed 24 hours later by placing the animal on the runway and again evaluating the latency in entering the chamber, using an end-point of 300 s (cfr. Bammer, loc. cit.).

The results of each compound under examination were expressed as percentage of amnesia reversal in order to make comparisons across the tested compounds.

As described in Butler et al. (loc. cit.), two groups of control animals were used on each experiment: (1) a ceiling control group (no ECS or scopolamine plus placebo injection), to ensure that the training was successful and that untreated animals remembered the task; and (2) a base-line control group (ECS or scopolamine plus placebo), to ensure that ECS produced amnesia for the task in untreated animals.

Tipically, in this retention test 70–100% of the animals of the ceiling control group would remember the response and exhibit a latency to enter the darkened chamber higher than 250 s.

Consequently, an animal was regarded as being under amnesia whenever its latency to enter the darkened chamber during the retention test was less than 50% of the average time of the animals of the ceiling control group.

To assess amnesia reversal (AR), the equation employed was as follows:

$$\% \text{ amnesia reversal} = \frac{(\text{drug group}) - (\text{base-line control group})}{(\text{ceiling control group}) - (\text{base-line control group})} \times 100$$

If the base-line control group had more than 30% of the animals remembering the task, the data for the entire day was discarded. If there was not a separation between base-line and ceiling control groups of at least 40% correct retention, the data for the entire experiment was similarly discarded.

The data obtained are illustrated in the table. In particular at the dose of 100 mg/kg ST 635, ST 645 and ST 630 have activity comparable with that of Piracetam and Oxiracetam.

At a lower dose, i.e. 10 mg $Kg^{-1}$, Oxiracetam and Piracetam are substantially inactive, whereas ST 630 and ST 682 exhibit 72% and 69%, respectively, of amnesia reversal. ST 625 and ST 638 exhibit 43% and 37%, respectively, of amnesia reversal, and ST 650 34%.

(B) Behavioural profile

The behavioural profile was assessed in Swiss albino male mice weighing 22–24 g, using the Irwin test (IRWIN S., Drug screening and evaluative procedures. 136, 123–128, 1962). The animals had been caged under normal conditions and kept fasting for the last 18 hours. Following administration of the compounds, the behaviour of the animals was monitored for 6 hours.

The compounds ST 638 and ST 682 were suspended in 10% arabic gum and orally administered, respectively, at pH 6.3 and 4.6 at doses equimolar to 100, 25, 6, 1.5 mg/10 ml/kg oxiracetam.

Water solutions of the compounds ST 625, ST 630, ST 635, ST 645 and ST 650 were administered.

The animals of the control groups were administered 10% arabic gum (10 ml/kg, orally) or warer (10 ml/kg i.p.). 100 mg ST 638/kg, orally, reduced spontaneous motility and grip strength; moreover, this compound induced catalepsy.

These effects lasted 15 to 60 minutes. 25, 6 and 1.5 mg/kg orally increased spontaneous motility. This effect lasted 20 to 45 minutes. 100 and 25 mg ST 682/kg, orally, riduced the spontaneous motility in the first thirty minutes following treatment.

ST 625, ST 630, ST 635, ST 645 and ST 650 did not alter, at the tested doses, the behavioural profile.

(C) Analgesic activity

The analgesic activity was assessed in Albino Swiss mice weighing 22–24 g, utilizing the hot plate test (57° C.).

The animals, kept under normal caging conditions and kept fasting for 18 hours, were placed on the hot plate for 30, 60 and 120 minutes following the administration of 100, 25, 6 and 1.5 mg/10 ml/kg of each compound under examination.

The analgesic activity was assessed by measuring the increase (in seconds) of the time the animals continued to stay on the hot plate. None of the tested compounds was shown to possess analgesic activity, with the exception of ST 638 that, orally administered, increased the raction time from 30 to 120 minutes with respect to its own zerotime, in a statistically significant way.

The compounds of the present invention can be formulated into orally or parenterally administrable pharmaceutical compositions. Suitable excipients and compositions for tablets, vials and the like are illustrated in the afore-said Canadian patent 1,100,515.

Pharmaceutical compositions in unit dosage form comprise between about 100 and about 500 mg of active ingredient.

TABLE

| Passive avoidance following ECS-or scopolamine-induced amnesia: antiamnesic activity data of some compounds of formula (I). | | | | | | | |
|---|---|---|---|---|---|---|---|
| | ECS 100 mg Kg $^{-1}$ | | ECS 10 mg Kg $^{-1}$ | | ECS 1 mg Kg $^{-1}$ | | SCOPOLAMINA 1 mg Kg $^{-1}$ |
| | n° | % AA | n° | % AA | n° | % AA | n° | % AA |
| Ceiling control group | 92 | 100 | 540 | 100 | 540 | 100 | 350 | 100 |
| Base-line control group | 214 | 0 | 1018 | 0 | 1018 | 0 | 613 | 0 |
| Oxiracetam | 53 | 43 | 32 | 8 | 31 | 31 | 23 | 0 |
| Piracetam | 13 | 39 | 30 | 0 | 27 | 0 | 10 | 19 |
| ST 625 | 15 | 0 | 44 | 42 | 43 | 23 | 24 | 50 |
| ST 630 | 14 | 16 | 43 | 9 | 36 | 0 | 35 | 5 |
| ST 635 | 11 | 46 | ND | | ND | | ND | |
| ST 638 | ND | | 21 | 36 | 19 | 22 | 11 | 0 |
| ST 645 | 12 | 44 | 12 | 14 | 12 | 30 | 12 | 0 |
| ST 650 | ND | | 25 | 34 | 26 | 35 | 18 | 32 |
| ST 682 | ND | | 24 | 51 | 11 | 2 | ND | |

What is claimed is:

1. (Pyrrolidin-2-one-1-yl)acetamides of general formula (I)

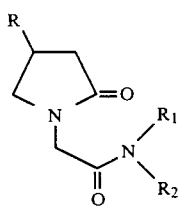

wherein R is hydrogen or hydroxyl, $R_1$ is hydrogen, $R_2$ is selected from the group consisting of:
2-aminoethyl,
2-(N,N-diisopropyl)aminoethyl,
3-(pyrrolidin-2-one-1-yl)propyl,
2-[N-(pyrrolidin-2-one-1-yl)acetyl]aminoethyl,
2-hydroxyethyl,
(glycerophosphorylethanolamino)carbonylmethyl,
1-trimethylammonium-3-carboxy-2-propyloxy-carbonyl methyl chloride,
(prolinol-1-yl)carbonylmethyl,
1-trimethylammonium-3-carboxyisopropyl, and
3-pyridylcarbamide;
or $R_1$ and $R_2$, taken together, are such as to form a ring of formula

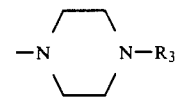

wherein $R_3$ is selected from the group consisting of phenyl substituted with halogens or halogen-substituted lower ($C_1$–$C_4$) alkyls and 4-morpholinocarbonylmethyl.

2. The compound of claim 1, wherein R is OH, $R_1$ is H and $R_2$ is 2-aminoethyl.

3. The compound of claim 1, wherein R is H, $R_1$ is H and $R_2$ is 2-aminoethyl.

4. The compound of claim 1, wherein R is OH, $R_1$ is H, and $R_2$ is 2-(N,N-diisopropyl)aminoethyl.

5. The compound of claim 1, wherein R is H, $R_1$ is H and $R_2$ is 3-(pyrrolidin-2-one-1-yl)propyl.

6. The compound of claim 1, wherein R is OH, $R_1$ is H and $R_2$ is 2-[N-(pyrrolidin-2-one-1-yl)acetyl]aminoethyl.

7. The compound of claim 1, wherein R is H, $R_1$ is H and $R_2$ is 2-hydroxyethyl.

8. The compound of claim 1, wherein R is H, $R_1$ is H and $R_2$ is (glycerophosphorylethanolamine)carbonylmethyl.

9. The compound of claim 1, wherein R is H, $R_1$ is H and $R_2$ is 1-trimethylammonium-3-carboxy-2-propyloxy-carbonylmethyl chloride.

10. The compound of claim 1, wherein R is H, $R_1$ is H and $R_2$ is (prolinol-1-yl)carbonylmethyl.

11. The compound of claim 1, wherein R is H, $R_1$ is H and $R_2$ is 1-trimethylammonium-3-carboxyisopropyl.

12. The compound of claim 1, wherein R is H and $R_1$ is H and $R_2$ is 3-pyridylcarbamide.

13. The compound of claim 1, wherein R is H and R1 and R2 taken together form 4-(morpholinocarbonylmethyl)-1-piperazyl.

14. The compound of claim 1, wherein R is H and R1 and R2 taken together form 4-(3-chlorophenyl)-1-piperazil.

15. The compound of claim 1, wherein R is H and R1 and R2 taken together form 4-(3-trifluoromethylphenyl)-1-piperazil.

16. An orally or parenterally administrable pharmaceutical composition for enhancing learning and memory which comprises as active ingredient a (pyrrolidin-2-one-1-yl) acetamide of general formula (I)

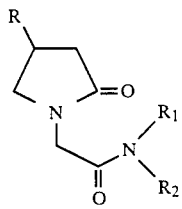

wherein R is hydrogen or hydroxyl, $R_1$ is hydrogen, $R_2$ is selected from the group consisting of:
2-aminoethyl,
2-(N,N-diisopropyl)aminoethyl,
3-(pyrrolidin-2-one-1-yl)propyl,
2-[N-(pyrrolidin-2-one-1-yl)acetyl]aminoethyl,
2-hydroxyethyl,
(glycerophosphorylethanolamino)carbonylmethyl,
1-trimethylammonium-3-carboxy-2-propyloxy-carbonyl methylchloride,
(prolinol-1-yl)carbonylmethyl,
1-trimethylammonium-3-carboxyisopropyl), and
3-pyridylcarbamide;
or $R_1$ and $R_2$, taken together, are such as to form a cycle of formula

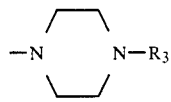

wherein $R_3$ is selected from the group consisting of phenyl substituted with halogens or halogens-substituted lower ($C_1$–$C_4$) alkyls and 4-morpholinocarbonylmethyl.

17. The pharmaceutical composition of claim 16 in unit dosage form, comprising from about 100 to about 500 mg of a compound of general formula (I).

* * * * *